United States Patent [19]

Szántay et al.

[11] Patent Number: 4,549,020

[45] Date of Patent: Oct. 22, 1985

[54] EBURNANE OXIME ETHERS

[75] Inventors: Csaba Szántay; Lajos Szabó; Gyorgy Kalaus; János Sápi; Mária Zájer nee Balázs, all of Budapest; Bela Kiss, Vecses; Elemer Ezer, Budapest; Egon Karpati, Budapest; László Szporny, Budapest, all of Hungary

[73] Assignee: Richter Gedeon Vegyeszeti Gyar Rt., Budapest, Hungary

[21] Appl. No.: 508,437

[22] Filed: Jun. 27, 1983

[30] Foreign Application Priority Data

Jun. 30, 1982 [HU] Hungary ............................ 2133

[51] Int. Cl.$^4$ ............................................. C07D 461/00
[52] U.S. Cl. ............................................................ 546/51
[58] Field of Search .......................... 546/51; 424/256; 514/283

[56] References Cited

U.S. PATENT DOCUMENTS

| | | | |
|---|---|---|---|
| 3,755,335 | 8/1973 | Thal et al. | 546/51 |
| 3,839,449 | 10/1974 | Herold | 564/256 X |
| 4,077,999 | 3/1978 | Budai et al. | 564/256 |
| 4,316,028 | 2/1982 | Katsube et al. | 546/51 |

FOREIGN PATENT DOCUMENTS

| | | | |
|---|---|---|---|
| 0765006 | 9/1971 | Belgium | 546/51 |
| 2085630 | 12/1971 | France | 424/256 |
| 2454808 | 12/1980 | France | 424/256 |

*Primary Examiner*—Donald G. Daus
*Assistant Examiner*—Diana G. Rivers
*Attorney, Agent, or Firm*—Karl F. Ross; Herbert Dubno

[57] ABSTRACT

The invention relates to optically active or racemic eburnane-oxime ethers of the formulae (Ia) and/or (Ib)

wherein
R represents an alkyl group having 1 or 2 carbon atoms,
$R^2$ represents an alkyl group having 1 to 6 carbon atoms, and the configuration of the hydrogen in the 3-position and the $R^2$ group is $\alpha,\alpha$ and/or $\beta,\beta$ or $\alpha,\beta$ and/or $\beta,\alpha$ and acid addition salts thereof.

The new compounds show valuable pharmaceutical activities, thus are potent CNS-tranquillants, smooth muscle relaxants, sedatives and hypnotic agents, and can therefore be employed as active ingredients of pharmaceutical compositions, which are also within the scope of the present invention.

3 Claims, No Drawings

EBURNANE OXIME ETHERS

The invention relates to new eburnane-oxime ethers, to a process for their preparation and to pharmaceutical compositions containing them. More particularly, the invention concerns new racemic and optically active eburnane-oxime ether derivatives of the formulae (Ia) and/or (Ib)

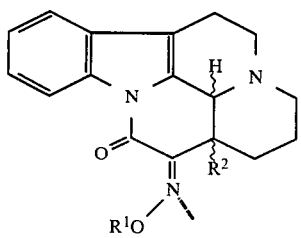

(Ia)

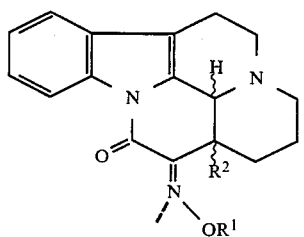

(Ib)

wherein
$R^1$ is alkyl having 1 or 2 carbon atoms,
$R^2$ is alkyl having 1 to 6 carbon atoms,
and the configuration of the hydrogen in the 3-position and
$R^2$ is $\alpha,\alpha$ and/or $\beta,\beta$ or $\alpha,\beta$ and/or $\beta,\alpha$ and acid addition salts thereof.

The invention further relates to a process for the preparation of said compounds of the formulae (Ia) and/or (Ib) and acid addition salts thereof, by alkylating racemic or optically active eburnane-oxime derivatives of the formulae (IIa) and/or (IIb)

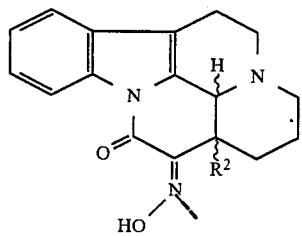

(IIa)

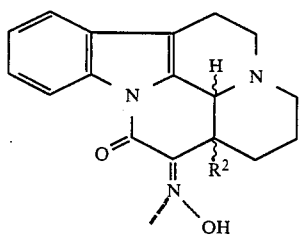

(IIb)

wherein $R^2$ and the configuration of the 3-hydrogen and $R^2$ have the same meaning as defined above, or acid addition salts thereof, and if desired, resolving the racemic compounds of the formulae (Ia) and/or (Ib) and/or if desired, treating the racemic or optically active compounds of the formulae (Ia) and/or (Ib) obtained by an acid.

The new compounds of the formulae (Ia) and/or (Ib) possess valuable pharmaceutical activities, thus are potent CNS-tranquilizers, smooth muscle relaxants, sedatives and hypnotic agents. The pharmaceutical compositions containing compounds of the formulae (Ia) and/or (Ib) or acid addition salts thereof as active ingredients are also within the scope of the invention.

In the above formulae $R^1$ and $R^2$ as alkyl groups having 1 or 2 and 1 to 6 carbon atoms, respectively represent straight or branched chain alkyl groups, e.g. methyl or ethyl and methyl, ethyl, n-propyl, isopropyl, n-butyl, sec-butyl, tert-butyl, n-pentyl, isopentyl, n-hexyl, isohexyl groups, respectively.

Starting compounds of the formulae (IIa) and/or (IIb) are new. They can be prepared from the corresponding eburnamonine derivatives by oximation, preferably carried out with a tertiary $C_{4-8}$-alkyl nitrite, in the presence of a strong base.

The alkylation of the racemic or optically active compounds of the formulae (IIa) and/or (IIb) can for example be accomplished with a suitable diazoalkane, preferably diazomethane or diazoethane. The process according to the invention is preferably performed in an organic solvent or solvent mixture inert under the reaction conditions, preferably in a mixture of an aliphatic alcohol and a halogenated aliphatic hydrocarbon, or in an aromatic hydrocarbon. The alkylation is preferably carried out at a reduced temperature, preferably between 0° C. and 5° C.

In the process according to the invention the configuration of the hydrogen in the 3-position and $R^2$ does not change, i.e. the configuration is the same in the end products of the formulae (Ia) and/or (Ib) as in the starting compounds of the formulae (IIa) and/or (IIb).

If desired, the compounds of the formulae (Ia) and/or (Ib) may be converted into their acid addition salts. Suitable acids for this purpose include inorganic acids such as hydrogen halides, e.g. hydrochloric acid, hydrogen bromide; sulfuric acid, phosphoric acid, nitric acid; perhaloic acids; e.g. perchloric acid, etc.; organic carboxylic acids, such as formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinnamic acid, benzoic acid, phenylacetic acid, p-amino-benzoic acid, p-hydroxy-benzoic acid, p-amino-salicylic acid, etc.; alkylsulfonic acids, such as methane-sulfonic acid, ethanesulfonic acid, etc.; cycloaliphatic acids, e.g. cyclohexylsulfonic acid, arylsulfonic acids, e.g. p-toluene-sulfonic acid, naphthylsulfonic acid, sulfanylic acid, etc.; amino acids, such as asparaginic acid, glutaminic acid, N-acetyl-asparaginic acid, N-acetyl-glutaric acid, etc.

The salts are generally prepared in an inert organic solvent, for example in an aliphatic alcohol having 1 to 6 carbon atoms by dissolving the racemic or optically active compounds of the formulae (Ia) and/or (Ib) in said solvent, adding the corresponding acid into the solution while the pH of the mixture becomes slightly acidic (pH 5–6) and subsequently separating the precipitated acid addition salt from the reaction mixture by a suitable method, e.g. by filtration.

The racemic compounds of the formulae (Ia) and/or (Ib) can be resolved by known techniques but optically active end product of the formulae (Ia) and/or (Ib) may also be prepared by starting from the corresponding otpically active compounds of the formulae (IIa) and/or (IIb). Racemic products of the formulae (Ia) and/or (Ib) are preferably prepared directly from the corresponding racemic starting compounds of the formulae (IIa) and/or (IIb) while the optically active compounds of the formulae (Ia) and/or (Ib) are preferably obtained starting from the corresponding optically active compounds of the formulae (IIa) and/or (IIb).

If desired, the racemic or optically active compounds of the formulae (Ia) and/or (Ib) or acid addition salts thereof may be subjected to further purification, e.g. recrystallization. The solvents used for recrystallization are selected in accordance with the solubility and the crystallizability of the compound to be recrystallized.

The active ingredient of the formulae (Ia) and/or (Ib) or pharmaceutically acceptable acid addition salts thereof can be converted into pharmaceutical compositions for parenteral or enteral administration by admixing them with solid and/or liquid carriers and/or further additives conventionally used in the preparation of pharmaceutical compositions. As a carrier for example water, gelatine, lactose, starch, pectine, magnesium stearate, stearic acid, talc, vegetable oils, e.g. peanut oil, olive oil, etc. can be employed. The compositions may be finished in the form of solid, e.g. tablets, lozenges, dragées, capsules, such as hard gelatine capsules, suppositories, etc. or liquid, e.g. oily or aqueous solutions, suspensions, emulsions, syrups, soft gelatine capsules, injectable oily or aqueous solutions or suspensions, etc. formulations. The quantity of the solid carrier can be varied within a wide range but preferably is about between 25 mg. and 1 g. The pharmaceutical compositions optionally contain also conventional pharmaceutical additives, such as preservatives, stabilizing, wetting, emulsifying agents, salts capable of adjusting the osmotic pressure, buffers, flavoring agents, aroma agents, etc. Optionally further pharmaceutically active compounds can also be present in the formulations.

The pharmaceutical compositions are preferably manufactured in dosage units, suitable for the desired route of administration. The pharmaceutical compositions may be prepared by conventional techniques, which comprise for example secreening, admixing, granulating, pressing or dissolving of the components. The compositions obtained can be subjected to further operations conventionally used in the pharmaceutical industry, for example sterilization.

Further details of the present invention are to be found in the following Examples which are, however, by no means intended to limit the scope of the protection sought.

EXAMPLE 1

Z-(+)-14-Oxo-15-methoxyimino-eburnane(3α,16α) and its hydrochloride 4.00 g. (12.4 mmoles) of Z-(+)-14-oxo-15-hydroxyimino-eburnane(3α,16α) are dissolved in a mixture of 40 ml. of methanol and 20 ml. of dichloromethane. To the solution obtained a solution of diazomethane, prepared from 2.8 g. of N-nitrozo-N-methyl-urea according to Vogel: Practical organic Chemistry, 3rd Edition, 971 in 60 ml. of dichloromethane is added at 0° C. and the reaction mixture is allowed to stand for 24 to 36 hours. The reaction is monitored by thin layer chromatography (KG-F$_{254}$, dichloromethane:methanol=20:1).

The R$_f$-value of the end product is higher than that of the starting material.

The solvent is eliminated in vacuum and the residual oil weighing 4.5 g. is dissolved in 15 ml. of methanol. The pH of the solution is adjusted to 2–3 by hydrochloric acid in methanol and it is allowed to crystallized. 3.23 g. of the hydrochloride of the named compound are obtained.

Yield: 69.7%

Melting point: 248° C. (decomp.)

$[\alpha]_{546}^{18} = +39°$; $[\alpha]_{578}^{18} = +37.5$ (c=1, chloroform).

IR spectrum (KBr): 1715 (CO), 1642 cm$^{-1}$ (C+N)

$^1$H-NMR (CDCl$_3$): 8.48–7.75 (4H, m, aromatic); 4.08 (3H,s, 3-H); 1.02 (3H,t,J=7.5 Hz, CH$_2$CH$_3$). Mass spectrum (m/3%): 337 (M$^+$, 100), 336 (63.5), 308 (47.7), 277 (24.2), 267 (18.2).

EXAMPLE 2

E-(−)-14-Oxo-15-methoxyimino-eburnane(3α,16α) and its hydrochloride 200 mg. (0.62 mmoles) of E-(−)-14-oxo-15-hydroxyimino-eburnane(3α,16α) obtained in a smaller amount by oximation of vincamone are reacted with 4 ml. of a solution of diazomethane in dichloromethane (preparation according to Vogel: Practical Organic Chemistry 3rd Edition, 971) in a mixture of 2 ml. of methanol and 1 ml. of dichloromethane at about 0° C., with stirring, for one and a half hours. The reaction is monitored by thin layer chromatography (KG-G, dichloromethane:methanol=20:1). The R$_f$-value of the end product is higher than that of the starting compound.

The solvent is eliminated in vacuum and the residue, weighing 240 mg. is purified by preparative layer chromatography (KG-60-PF$_{254+366}$, dichloromethane:methanol=100:6, elution with a 10:1 mixture of dichloromethane and methanol). By evaporation of the eluate 187 mg. (89.6%) of an oil product are obtained, which is then dissolved in 1.5 ml. of methanol. The pH of the solution is adjusted to 3 with hydrochloric acid in methanol and crystallization of the product is induced by adding 4 ml. of ether.

150 mg of the named compound are obtained as a hydrochloride.

Yield: 72.3%

Melting point: 190° to 192° C. (methanol)

$[\alpha]_{546}^{23} = -263°$ (c=−0.8, chloroform)

IR spectrum (KBr): 1675 (CO), 1640 cm$^{-1}$ (C+N).

Mass spectrum (m/e, %): 337 (M$^+$, 100).

$^1$H-NMR spectrum (CDCl$_3$): 8.46–7.30 (4H, m, aromatic); 4.45 (1H,s,OCH$_3$); 4.26 (1H,s,3-H), (3H,t,J=7.2 Hz, C—CH$_2$—CH$_3$).

We claim:

1. A compound of the formulae (Ia) or (Ib)

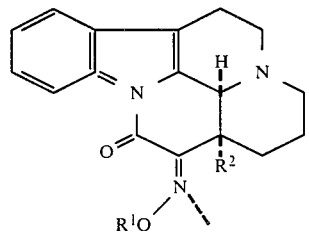

-continued

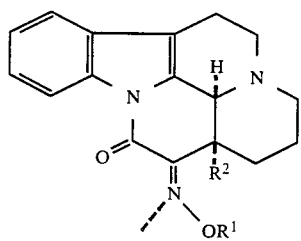

(Ib)

in which
R¹ represents an alkyl group having 1 or 2 carbon atoms, and
R² is ethyl or an acid addition salt thereof.

2. The compound defined in claim 1 which is Z-(+)-14-oxo-15-methoxyimino-eburnane(3alpha,16alpha) or a pharmaceutically acceptable acid addition salt thereof.

3. The compound defined in claim 1 which is E-(−)-14-oxo-15-methoxyimino-eburnane(3alpha,16alpha) or a pharmaceutically acceptable acid addition salt thereof.

* * * * *